United States Patent
Unsworth et al.

(10) Patent No.: US 6,615,080 B1
(45) Date of Patent: Sep. 2, 2003

(54) NEUROMUSCULAR ELECTRICAL STIMULATION OF THE FOOT MUSCLES FOR PREVENTION OF DEEP VEIN THROMBOSIS AND PULMONARY EMBOLISM

(76) Inventors: John Duncan Unsworth, c/o Vasotech Corp. 7 Innovation Drive, Suite 107, Flamborough, Ontario (CA), L9H 2H9; Jack Hirsh, 21 Cottage Avenue, Hamilton, Ontario (CA), L8P 4G5; Robert Edward Kaplan, 69 Dorchester Rd., Buffalo, NY (US) 14222; James Joseph Czyrny, 21 Snyderwoods Ct., Amherst, NY (US) 14226

( * ) Notice: Subject to any disclaimer, the term of this patent is extended or adjusted under 35 U.S.C. 154(b) by 30 days.

(21) Appl. No.: 09/819,678
(22) Filed: Mar. 29, 2001
(51) Int. Cl.[7] ................................................. A61N 1/00
(52) U.S. Cl. ............................................................ 607/2
(58) Field of Search ............................ 607/1, 2, 48, 49, 607/144, 72–76

(56) References Cited

U.S. PATENT DOCUMENTS

| | | |
|---|---|---|
| 2,003,392 A * | 6/1935 | Rucker |
| RE32,940 E | 6/1989 | Gardner |
| 5,358,513 A | 10/1994 | Powell, III |
| 5,407,418 A | 4/1995 | Szpur |
| 5,556,422 A | 9/1996 | Powell, III |
| 5,643,331 A | 7/1997 | Katz |
| 5,674,262 A | 10/1997 | Tumey |
| 5,782,893 A | 7/1998 | Dennis |
| 5,891,065 A | 4/1999 | Caripa |
| 6,002,965 A | 12/1999 | Katz |

* cited by examiner

*Primary Examiner*—Scott M. Getzow (57) ABSTRACT

A single channel neuromuscular electrical stimulation (NMES) device for the prevention of deep vein thrombosis (DVT), pulmonary embolism (PE), lower extremity edema, and other associated conditions by electrical stimulation of the muscles of the foot muscles. An electrical signal generator produces a square wave pattern of variable frequency, duration, intensity, ramp time, and stimulation on-off cycle. Surface electrodes are positioned over the foot muscles and are attached to the stimulator by various means. The stimulator is programmed in a manner to stimulate the foot muscles to reduce pooling of the blood in the soleal veins of the calf This is accomplished by only stimulating the soles of the feet.

25 Claims, 6 Drawing Sheets

NEUROMUSCULAR ELECTRICAL STIMULATION OF THE FOOT MUSCLES FOR PREVENTION OF DEEP VEIN THROMBOSIS AND PULMONARY EMBOLISM

FIELD OF THE INVENTION

This invention relates to the use of single channel Neuromuscular Electrical Stimulation (NMESS) of the lower extremity for the prevention of Deep Vein Thrombosis (DVT) and Pulmonary Embolism (PE) by reducing the pooling of blood in the soleal veins of the calf.

BACKGROUND OF THE INVENTION

Venous thromboembolic disease (VTED) continues to be a cause of significant morbidity and mortality for individuals immobilized during prolonged travel, after orthopedic surgery, neurologic disorders, and a variety of other conditions.

Virchow in 1845, postulated that changes in blood flow, vessel wall, and blood constituents were responsible for venous thrombosis.[1] Studies have shown that at least two of the three factors are nee de d to trigger thrombosis. Reduction of blood flow, especially in the venous sinuses of the calf muscles has long been recognized as an important risk factor.[2,3,4] The venous pooling triggers coagulation and at the same time consumes local anticoagulants. This explains the high risk of DVT and PE in spinal cord injury, stroke, and post-surgery where immobility of the lower limbs occurs.

Homans[5] observed in 1954 that "prolonged dependency stasis, a state imposed by airplane flights, automobiles trips and even attendance at the theater, is able unpredictably, to bring on thrombosis . . . " Until recently it was not known if only travel, without other risk factors, was sufficient to cause venous thrombosis. In 1977, Symington[6] showed that trips as short as three to four hours can induce deep vein thrombosis (DVT) and pulmonary embolism (PE), although longer trips are more usual. In 1999, Ferrari[7] demonstrated that, in people over 50 years of age, a history of recent travel is a risk factor by itself for thromboembolic disease. He further confirmed that travel longer than four hours increased the risk by four times, even in healthy individuals over 50 years of age. With the decreased legroom in airliners and the escalating time spent in the cramped situation of economy class, Cruickshank coined the term Economy Class Syndrome for the increasing travel-associated venous thromboembolic disease (VTED).[8]

In travel associated VTED additional risk factors include pressure on the calves from the back of a seat exacerbating venous stasis,[9] dehydration,[10] hemocentration,[11] and a decrease in fibrinolysis.[12]

Current approaches to prophylaxis include mechanical compression using pneumatic compression devices, and anticoagulation therapy. While both have demonstrated effectiveness, they have problems as well. Pneumatic compression equipment is clearly too cumbersome for mobile patients, or during prolonged travel. In addition, AC current is required for these devices and is not practical for these conditions. No manufacturer has designed a battery-operated device. Even if this were done, the battery would be too large and heavy to provide the needed electric current for more the six hours.

Anticoagulation therapy carries the risk of bleeding complications and must be started several days in advance to be effective.

Electric stimulation has theoretical advantages in that it can be started at the time prophylaxis is needed, and can be portable using DC current sources. Previous studies have shown that electrical stimulation is an effective means of increasing venous blood flow and preventing DVT. Nicolaides et al[13] studied 116 patients undergoing different operations under general anesthesia. An AC-operated Thrombophylactor supplied single impulse in square waveform. The intensity was strong enough to produce "brisk plantar flexion of the foot without violent movement of the leg". This stimulation was discontinued at the end of the operation just before the patient woke up. It was found that a resting period less than 4 seconds did not allow the soleal veins to fill completely before the next stimulus and resulted in a progressive reduction in stroke volume from the calf muscles. On the other hand, a resting period longer than 5 seconds allowed the soleal veins to fill in the interval between stimuli, resulting in the maximum stroke volume. The optimum rate of stimulation was found to be 12–15 per minute and optimal duration of 50 milliseconds. This stimulus parameter produced the greatest improvement in femoral venous Doppler blood flow. It was shown by a 92% relative reduction in DVT incidence as determined by $^{125}$I-fibrinogen testing.

Lindstrom et al[14] used groups of stimuli to produce a short-lasting tetanus vs. single stimulus on ten patients being operated on for various abdominal diseases. The aim of the study was to investigate whether a summation of contractions by grouped impulses was more efficient than a single impulse in reducing venous stasis. All patients were anaesthetized during the study. A Whitney strain gauge plethysmograph was used to record changes in calf volume during stimulation. Two surface electrodes were attached just below the knee joint and above the ankle on the back of the leg. A stimulator was used to deliver a square waveform, which could be varied in duration, amplitude and frequency. It was found that this short tetanus reduced calf venous volume three times more effectively than single stimulus. The strength of individual impulses was of the order of 40–50 mA. Using a stimulus duration of 50 milliseconds, they found that grouped stimuli at 8/min, 6 impulses/group and 8 impulses/second were most efficient at reducing venous volume as recorded by plethysmograph. In this study, a lower frequency of 8 grouped impulses per minute was used instead of 12–15 single impulses per minute as advocated in the Nicolaides study.

Merli et al[15] performed a prospective study of DVT prophylaxis in acute spinal cord injury (SCI) patients. In the study 48 patients were randomly assigned to saline placebo, subcutaneous low dose heparin or heparin with ES for 23 hours per day over 28 days. Stimulus parameters included a frequency of 10 Hz, duration of 50 microseconds, cycle of 4 seconds "on" and 8 seconds "off". Both tibialis anterior and gastrocnemius muscles were stimulated to produce a moderately strong contraction. Surveillance for DVT was evaluated by daily 125-I fibrinogen scanning. A significant decrease in the incidence of DVT was noted in the subcutaneous heparin with ES group, but not in the group with placebo or heparin alone.

Jaweed et al[16] studied the effects of ES in enhancing femoral venous flow in six normal subjects. A square wave with stimulus duration of 200 microseconds was given at frequencies of 2, 5 and 10 Hz in 2 to 3 sessions over four weeks. Maximum peak velocity was measured bilaterally in the supine posture. It was found that electrical stimulation (ES) at 10 Hz significantly increased femoral venous flow but not at lower frequencies of 2 and 5 Hz.

There a number of U.S. patents that teach methods of applying electrical stimulation for the prevention of DVT. These include the following patents: the Powell, III patent, U.S. Pat. No. 5,358,513; the Tumey patent, U.S. Pat. No. 5,674,262; the Dennis, III patent, U.S. Pat. No. 5,782,893; the Katz patent, U.S. Pat. No. 5,643,331; and the more recent Katz patent, U.S. Pat. No. 6,002,965. What these patents have in common is that they all describe methods of electrically stimulating the calf muscle.

These methods do enhance blood flow by causing the calf muscle to contract. But they also have some drawbacks that the present invention overcomes.

Positioning the electrodes on the calf muscle can be problematic. The differences in size and shape of peoples calf muscles requires fitting cuffs to ensure accurate placement of the electrodes. Often these electrode presenting cuffs or bands shift or slide down the leg with use. One irritating problem is the removal of the electrode from the calf when the hair on the leg becomes bound to the sticky electrode Another difficulty with these calf stimulators is that the fatty tissue layer has a relatively high resistance to electric current. This fatty surface layer, between the electrode and the muscle beneath, requires higher current settings in order to adequately stimulate the muscle to contraction. These higher current settings, especially with obese patients, can cause significant discomfort to the skin area around the electrode.

The size of the calf muscle also requires a relatively high current setting to cause it to contract. Again, higher current pulses are more likely to cause sensations that the user finds unpleasant, especially when administered over a long period of time.

What is need therefore is method of enhancing blood flow in the lower leg without the problems associated with stimulating the calf muscle.

What is also needed is a device that can be put on effortlessly, without fitting or adjustments, that doesn't shift or slip out of place during use.

What is also required is a device that is not uncomfortable to use, and is in fact pleasurable to use.

What is also needed is a device that can be used by obese patients who are at greatest risk for acquiring DVT.

A significant number of DVT cases occur on extended airplane flights where having a pleasurable experience, convenience of application, speed of fitting and removing, are all essential to their wide-scale adoption and use.

The present invention comprises a method and a device for preventing DVT by electrically stimulating the foot muscles by applying one electrode over or proximal to the heel and the other over the intrinsic muscles on the plantar surface of the foot, or proximal to them, for example on or around the ball of the foot.

This method and the preferred embodiments of the invention, described herein, have the advantage of: locating the electrodes where there is little or no body hair to become entangled in the sticky electrodes; locating the electrodes where there is little fat tissue, even in obese users; being applied by simply putting on an article of footwear; requiring only a few different sizes for virtually all users; being placed in close proximity to the muscle that is being stimulated; and being a pleasure to use. Because the physiology of the foot is relatively uniform among the population, compared to marked differences in calf size and fatty content, the method has the additional advantage in that the NMES unit that delivers the electrical current can be made to have a relatively narrow range of intensities to ensure that users will not inadvertently use a setting that would otherwise cause them pain.

The fact that the electrical stimulation of the foot would have the effect of enhancing blood flow in the calf and thus help prevent deep vein thrombosis and related maladies is quite unexpected. For example, the Tumey patent, U.S. Pat. No. 5,674,262, referred to above, coupled electrical stimulation of the calf muscle with pneumatic compression of the foot, rather than electric stimulation of the foot. It has not heretofore been understood that by electrically stimulating such a small group of muscles that blood flow could be enhanced thereby reducing the pooling of the blood in the soleal veins of the calf.

Two of the inventors, Kaplan and Czyrny, performed a trial study on two normal subjects and one obese subject between the ages of 50 to 80. The subjects were seated in chairs placed at a fixed distance apart. One lower limb was randomly selected for stimulation, therefore each subject served as his own control. Unlike previous studies where electric stimulation was applied to the calf muscles, surface electrodes were placed over the intrinsic muscles on the plantar surface of the foot, or proximal to them, for example on or around the ball of the foot, and over or proximal to the heel. Also, compared to those previous studies, a much lower intensity of stimulation was used.

For the method that is the subject of this invention, the intensity of the electrical stimulation required is only that necessary to create a slight visible muscle twitch of the foot muscles, or to put it another way a minimally visible or palpable muscle contraction. Previous studies used stimulus intensities much greater such that a vigorous muscle contraction was produced.

Kaplan and Czyrny measured Popliteal (calf) venous blood flow bilaterally using a Doppler ultrasound device at 0, 15, 120 and 240 minutes after stimulation began. The Doppler ultrasound evaluator was blinded as to the limb stimulated. Patients were also asked to fill out a brief questionnaire regarding their acceptance and tolerance of the electrical stimulation. The results of those tests demonstrated a significant increase in popliteal (calf) venous blood flow velocity across the 4-hour stimulation period for the stimulated leg during the majority of time frames measured. This is consistent with reduced venous pooling in the soleal veins of the calf It should be noted that the soleal veins refer to the plexus of veins located within the calf muscles. The term is not related to the sole of the foot.

Review of the patient questionnaires revealed excellent acceptance and tolerance of the electrical stimulation that was used in the study. The degree of tolerance was significantly greater than a previous study Kaplan and Czyrny performed looking at the tolerance of electrical stimulation of the calf muscles. Therefore it is believe that a mild electrical stimulation of the foot muscles is an effective, and well tolerated method of enhancing popliteal venous blood flow. Further studies will be required to fully elucidate the method and its application to various types of users and extended periods of use.

PRIOR ART STATEMENT

The articles listed herewith represent literature relating to electrical stimulation of leg muscles to inhibit deep venous thrombosis.

1. Virchow R. Ein Vortrag Uber die Throm bose vom Jahre 1845. In: Virchow R, ed. Gesammelte Abhandlungen Zur weissenschaftlichen Medizin. Frankfurt: Meidinger, 1845: 478–86.
2. Simpson K, Shelter. Death from pulmonary embolism. Lancet 1940; ii: 744.
3. Ledermann J A, Keshavarzian A. Acute pulmonary embolism following air travel. Postgrad Med J 1983; 39: 348–53.
4. Mammen E F. Pathogenesis of venous thrombosis. Chest 1992; 102(suppl): 640s–644s.
5. Homans J. Thrombosis of deep leg vein due to prolonged sitting. N England J Medicine 1954; 250: 148–9.
6. Symington I A, Stack B H R. Pulmonary thromboembolism after travel. Br J Dis Chest 1977,71: 138–40.
7. Ferrari E, Chevallier T, Chapelier A, Baudouy M. Travel as a risk factor for venous thromboembolic disease: a case-control study. Chest 1999; 115:440–444.
8. J Cruickshank, R. Gorlin, B. Jennett. Air travel and thrombotic episodes: the economy class syndrome. Lancet, August 1988.
9. Thomas J E P, Abson C P, Caims N J W, Pulmonary embolism. A hazard of air travel. Cent Air J Med 1981; 27: 85–87.
10. Simon R, Krol J. Jet "leg", pulmonary embolism and hypoxia (letter). Lancet 1996; 348: 416.
11. Moyses C. Economy class syndrome (letter). Lancet 1988; 1: 1077.
12. Gertler J P, Perry L, L'Italien G, et al. Ambient oxygen tension modulates endothelial fibrinolysis. J Vas Surg 1993; 18:939–946.
13. Nicolaides A N, Kakkar V V, Field E S, et al. Optimal electric stimulus for prevention of deep vein thrombosis. Br M J 1972; 3: 756–758.
14. Lindstrom B, Korsan B K, Jonsson, et al. Br J Surg 1982; 69: 203–206.
15. Merli G J, Herbison G J, Ditunno, et al. Deep vein thrombosis: prophylaxis in acute spinal cord injured patients. Arch Phys Med Rehab 1988, 69:661–664.
16. Jaweed M M, Herbison G J, Merli G, et al. Enhancement of venous blood flow velocity by low frequency electrical stimulation in normal human subjects. Arch
17. Phys Med Rehab 1986; 67: 61 (abstract)

SUMMARY OF THE INVENTION

The invention is comprised of a method for preventing DVT, ankle edema and venostasis and a device that includes a single channel sequential neuromuscular electrical stimulation (NMES) unit. The NMES unit 10 can be any NMES unit that is battery powered, compact and can be programmed to deliver the stimulus profile described below or such other profile that is found to be efficacious, such as the Focus™ manufactured by Empi Inc., 599 Cardigan Road St. Paul, Minn., U.S.A. In order to simplify the patient's ability to properly apply the NMES device, the stimulator generates biphasic symmetrical square wave pulses with stimulus parameters that our study demonstrated to result in optimum venous blood flow. The stimulus frequency is fixed at 50 pulses per second, the stimulus duration is set at 300 microseconds, the ramp up time at 2 seconds, the ramp down time at 2 seconds, and the stimulus cycle set at 12 seconds on and 48 seconds off. Once set in advance by the Doctor, manufacturer or user, the only adjustment necessary on the part of the patient is a stimulus intensity dial. This allows for a current up to 20 milliamperes to be delivered. The user adjusts the intensity to the point needed to produce a minimally visible or palpable muscle contraction. The output leads of the stimulator are attached through a conductor to electrodes of various types including, self-adherent surface electrodes. These electrodes being of opposite polarity and creating an electrical potential difference between themselves and the tissue that separates them.

While the type of electrical pulse generating unit and those characteristics and routine for administering the pulses described above have been found to be very effective in increasing blood flow, it is to be understood that any pulse generator that causes the foot muscle to periodically and gently contract, such that the user does not experience excessive pain, is within the ambit of the invention herein disclosed.

The unique feature of the invention is the use of a pre-programmed single channel stimulator that delivers a very mild, well-tolerated intensity that results in a mild contraction of the foot muscles. This is accomplished by only stimulating the soles of the feet. The surface electrodes were placed over intrinsic muscles on the plantar surface of the foot, or proximal to them, for example on or around the ball of the foot, and over or proximal to the heel. By stimulating in this manner, blood pooling in the calf veins is prevented. Preliminary studies by two of the inventors, Kaplan and Czyrny, using Doppler ultrasound techniques have shown that this method may be as effective as stimulation of the calf muscle group en masse as other devices do, and significantly better tolerated than these devices.

But in order for the method to work effectively and be self-administered without supervision and with minimal instructions, the placement of the electrodes and the type of electrodes used are critical. Elderly patients, who often have impaired abilities to self-administer treatments are the very ones that would benefit most the method that is herein described. The means for positioning the electrodes on the foot must therefore be convenient and effective.

The preferred embodiments of the invention include footwear and accessories to footwear that incorporated NMES devices and electrodes that can be used with or without socks and stockings. Some of the preferred embodiments lend themselves to one time use, such as would be the case for those used in airplane travel.

BRIEF DESCRIPTION OF THE DRAWINGS

FIGS. 7c, 7d and 7e illustrate how the NMES device 10 clamps the side of the article of footwear 15 and slides down the slider 18 to snuggly fit the side of the said article of footwear.

DESCRIPTION

Figure 1:
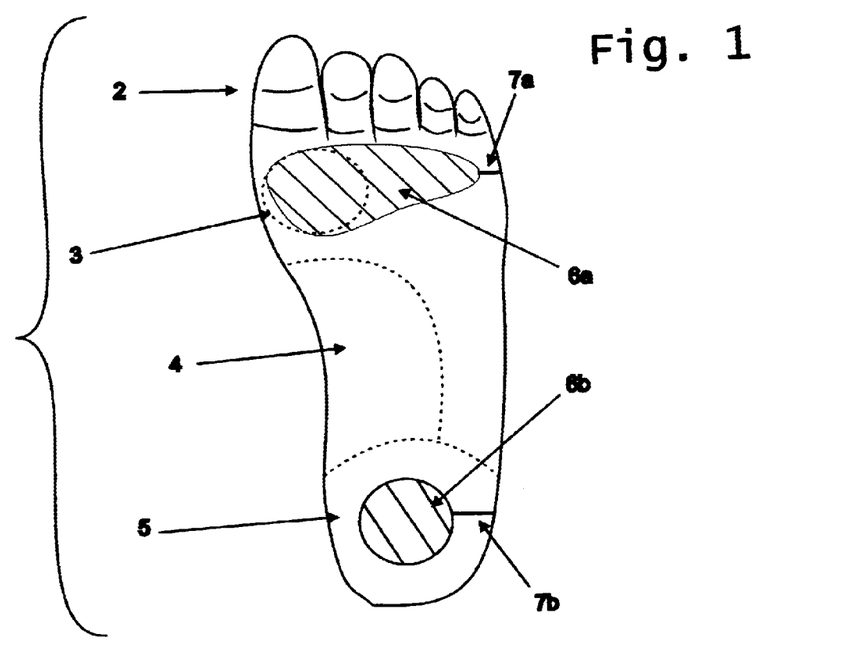
FIG. 1 is a perspective view that illustrates the location of the electrodes on the sole of the foot 6a, 6b, that being on the area over intrinsic muscles on the plantar surface of the foot, or proximal to them, for example on or around the ball of the foot 3, and over or proximal to the heel 5.
Figure 10:
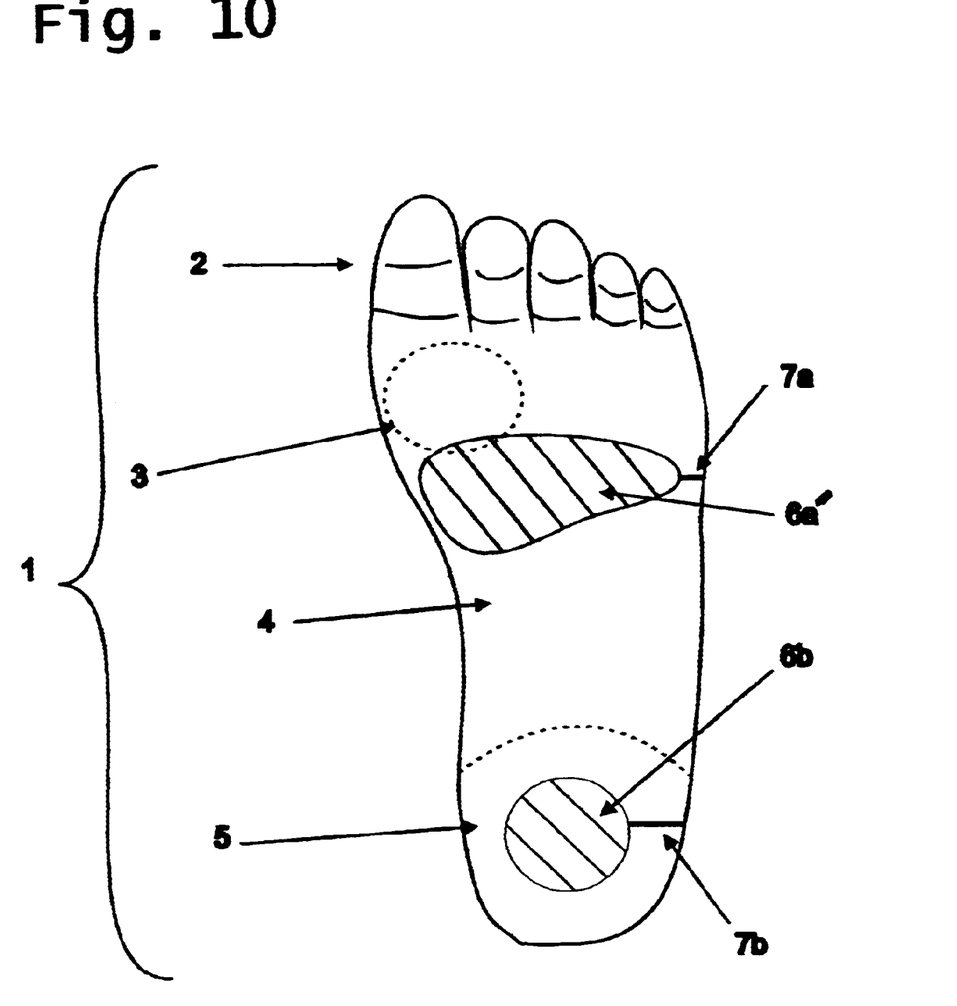
FIG. 10 illustrates the location of the electrodes on the sole of the foot 6a', 6b according to another preferred embodiment of the invention, in which area 6a' is an alternate preferred location of an electrode over intrinsic muscles on the plantar surface of the foot, or proximal to them.

FIG. 1 illustrates the areas of the bottom of the foot where the electrodes 6a and 6b are placed that deliver the electrical impulses generated by the NMES device 10. It is to be understood that these are approximate locations and sizes of electrodes and preferred embodiments of the invention will be of different sizes and shapes, and still come within the ambit of the invention. For example, FIG. 10 shows an alternate preferred area 6a' at which an electrical impulse can be delivered. In some preferred embodiments of the invention the electrode 6a occupies only the area of the ball of the foot, while other preferred embodiments are elliptical in shape, having their major axis normal to the longitudinal axis of the foot 1.

In all preferred embodiments of the system and devices that are described herein and that effect the method which, together with those devices forms the subject matter of this invention; have electrodes placed on a "platform" 21 with which the user's foot is in substantial contact, which includes contact separated by a garment or material such as a sock or stocking. This platform 21 can be the sole of a shoe, slipper, sock, stocking, any other item of footwear or it can be the part of an item that is inserted into any such item of footwear that contains electrodes, as described herein. It is to be understood then that the planar surface on which the electrodes are attached or detachably attached and that come into contact with the bottom of the user's foot directly or by some part of the electrode is a "platform" 21 for the purposes of this patent.

Figures 2, 3:
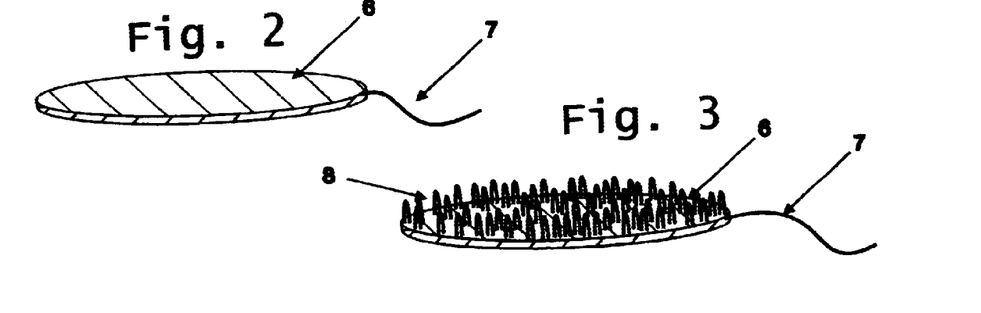
FIG. 2 is a perspective view that illustrates the conventional self-adhering electrode 6 with conductor 7.
FIG. 3 is a perspective view that illustrates means for maintaining electrical contact between the electrode and the user's foot, through an interposing sock or stocking
Figure 4A:
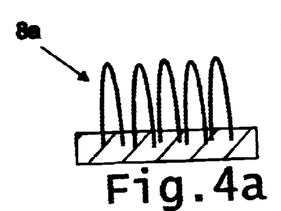
FIG. 4a, 4b and 4c are perspective views that illustrate additional embodiments of the invention that includes means for maintaining electrical contact between the electrode and the user's foot, through an interposing sock or stocking.
Figure 4B:
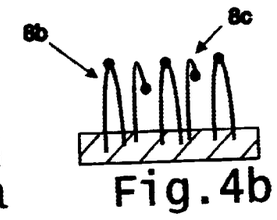
Figure 4C:
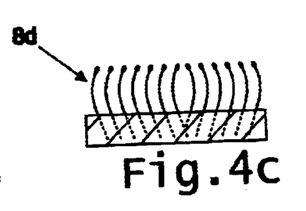

The electrodes in some preferred embodiments of the invention are the standard self-adhering, and somewhat sticky electrodes that are generally used for such purposes, as illustrated in FIG. 2 The electrodes 6a and 6b can be fabricated from a conducting foil and a conducting hydrogel adhesive, or from any other suitable conducting medium or could be on of myriad conventional electrodes currently being utilized for transcutaneous electro-neural stimulator units (TENS) devices such as those produced by the 3M company. While this type of electrode is acceptable for some preferred embodiments, sometimes the user would prefer to put on and take off the stimulator, without taking off and putting on his socks or stockings. One preferred embodiment of the invention includes electrodes that maintain electrical contact with the skin through fabric or other porous materials. FIG. 3 illustrates an electrode with rounded loops that are made of any electrically conductive material. Many metals and metal alloys, well known to the art, are suitable conductors for such a purpose. The hoops would be sufficiently narrow and long to project through the fabric and maintain contact with the skin. These hoops might also be coated with the same sticky material that is used on the normal self-adhering electrode to ensure the contact between hoop and skin is maintained. The base of the electrode could also be made of the same said self-adhering electrode material as is generally used in conventional electrodes. This would maintain an even charge between the hoops and also maintain contact with the interposing material, for example, a sock. The hoops being rounded would not irritate the skin, and being flexible would bend before piercing the skin. The number of hoops would vary and would be sufficiently numerous to maximize the surface area in contact with the skin, while at the same time not being so numerous that they would not pass through the interposed material. FIG. 4a is a detailed drawing of the hoop arrangement illustrated in FIG. 3. FIG. 4b is the same as FIG. 4a except that included with the hoops 8b are some hooks 8c which act to assist in holding the interposing material. The preferred embodiment illustrated in 8d is made of springy electrically conductive members, with rounded distal ends, perhaps coated with conductive self-adhering material. The preferred embodiment illustrated in 8d also includes bends or curves in the said members that ensure that they do not pierce or stick in the skin, even when pressed against the skin with the full weight of a person. The curved shapes of these electrodes also causes them to slide between the interposing material and the skin and thus increase the electrical contact between the electrode and the skin. As illustrated in FIG. 4c preferred embodiment of the invention can orient the curve in different directions to ensure the curved members pass through the interposing material, even when, for example, a foot slides into a shoe containing such an electrode, at a shallow angle of attack.

FIG. 5, 6, 7, 8 and 9 all illustrate preferred embodiments of the invention and more particularly means whereby the position of the electrical contacts are maintained against the ball and heel of the foot in that manner illustrated in FIG. 1. The preferred embodiments differ only in details of placing the NMES device and the issue of whether a material piercing electrode is necessary by the interposition of material such as a sock or stocking. It is to be understood that these preferred embodiments of the invention are only meant to be examples of the principal features of the invention. Each of the illustrations contain features of preferred embodiments, but it is to be understood that some of these features could be incorporated into the other preferred embodiments and features deleted from those preferred embodiments or both. While the illustrations show one foot it is to be understood that for most applications each foot will have its own NMES unit 10.

Figure 5:
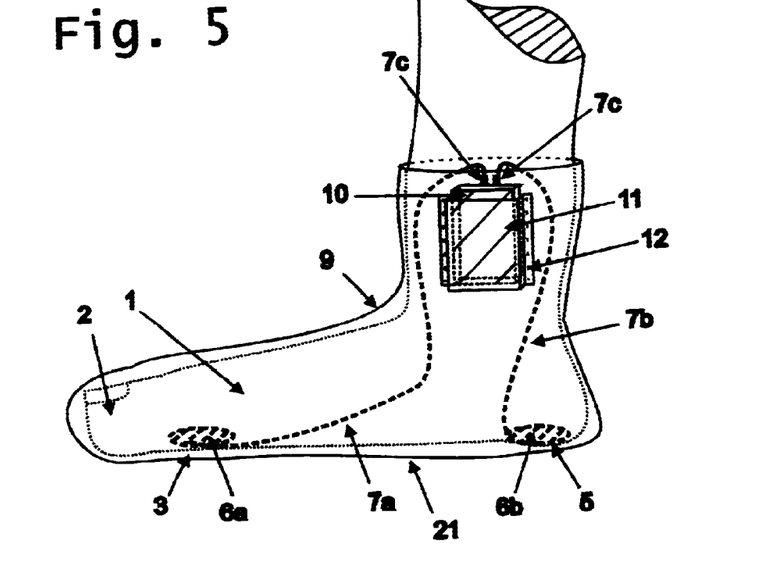
FIG. 5 is a perspective view that illustrates a preferred embodiment of the invention that locates the NMES device 10 in a pocket or pouch in a item of footwear, with conductors connecting the said NMES device to two electrodes placed beneath the heel and the area around the ball of the foot.

FIG. 5 illustrates an item of footwear which could for example be a sock, slipper or shoe. The conductors 7a and 7b can be partly or completely incorporated into the material from which the footwear is fabricated, attached to it or be completely or partly separate from it. The said conductors 7a and 7b connect the electrodes 6a and 6b to the NMES unit 10. The connection of the conductors 7a and 7b at the NMES unit 10 is usually by means of a standard plug connector 7c. The contacts 6a and 6b for this preferred embodiment would be the standard disposable self-adhering electrodes. These electrodes 6a, 6b could be separate from the said item of footwear 9 or it could be incorporated into it, in which case the footwear would likely be disposable. The said electrodes 6a and 6b would be placed in a similar manner as the preferred embodiment of the invention illustrated in FIG. 1. The NMES unit 10 in this preferred embodiment is placed in a pocket or pouch 11 that is attached to by standard fastening means 10 or incorporated into the material of the footwear 9. But another preferred embodiment might detachably attach the said NMES unit 10 to the footwear 9 using a patch of hook or loop material, attached to the said NMES unit 10, and a complementary patch of loop or hook material being attached to the said footwear 9, or forming part of the said footwear.

Figure 6:
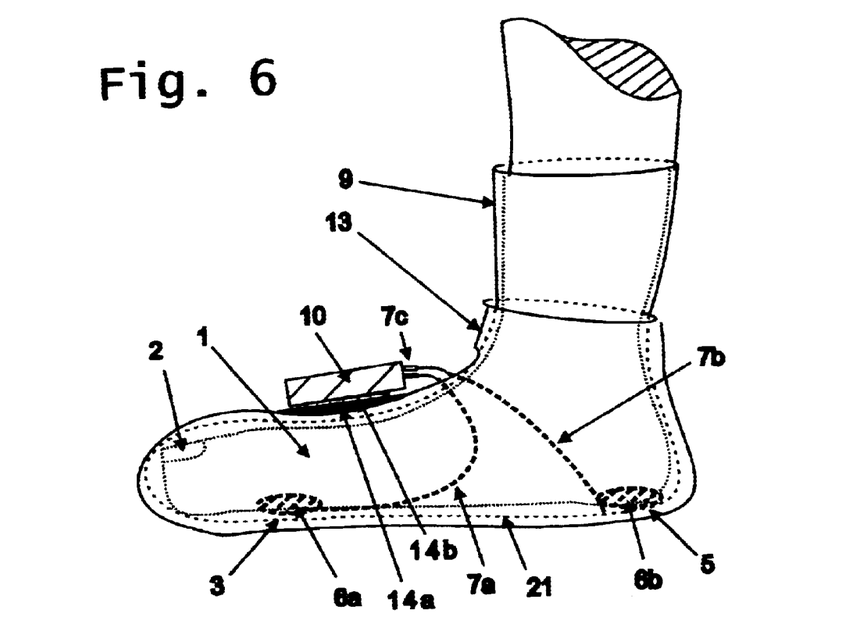
FIG. 6 is a perspective view that illustrates a preferred embodiment of the invention that locates the NMES device 10 on the top of the foot, and attaches it to an item of footwear with a complementary hook and loop material 14a, 14b, such as VELCRO.

FIG. 6 illustrates a preferred embodiment of the invention where the NMES unit 10 has been located on the top of the foot, where it is less likely to be brushed into something in the course of walking. It also has the advantage of being easy to see and easy to adjust, which is in contrast to the devices that are attached to the upper calf muscle, often under clothing. In this preferred embodiment the NMES unit 10 is detachably attached to the footwear 13 with complementary patches 14a, 14b of hook and loop fastener material, one of course being more permanently attached to the NMES unit 10 and the other to the footwear 13. The footwear can be of any type and can be worn with or without socks or stockings. If worn with stockings the footwear would have incorporated into them electrodes that could project through the material of the sock or stocking, such as those illustrated in the preferred embodiments of FIG. 4a, 4b and 4c. The use of these projecting electrodes allows the footwear to be readily put on and taken off with the utmost of ease and convenience. The material from which the footwear 13 is made could be partly or completely elastic which would assist in pressing the electrodes against the bottom of the foot. This feature is once that any preferred embodiment of the invention could include. In some applications this footwear would be disposable. For example the footwear 13 might be a disposable slipper given to an airplane passenger with NMES attached. The passenger would take his shoes off, and put the slippers on, adjust the intensity setting to the level that just gently contracts the foot muscles, relax and enjoy the gentle foot message. At the end of the trip the NMES unit could be removed by pulling away the hook and loop detachable attachments 14a and 14b and removing the two connectors 7c. The slipper could then be disposed of and the NMES unit 10 be retained for the next passenger. If however the footwear 13 is worn without a sock or stocking, it is possible that it would function and have those features as that preferred embodiment illustrated in FIG. 5, above. If worn without a sock or stocking, the footwear illustrated in FIG. 6 could have the standard self-adhering disposable electrode either incorporated into the footwear, in which case it would likely be disposable, or be separate, in which case only the electrodes likely would be disposed of after each use. Again the conductors 7a and 7b could be partly or completely incorporated into the material of the footwear 13 or be partly or completely separate.

Figure 7A:
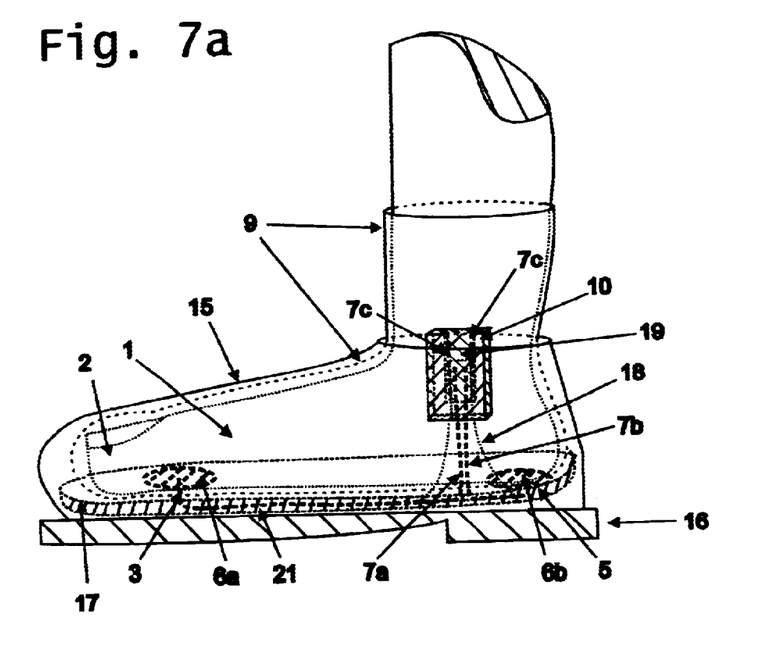
FIG. 7a and 7b are perspective views that illustrate an insert into an article of footwear, that locates the NMES device 10 on an adjustable slider that permits the said device to be clipped on the side of an article of footwear, while maintaining electrical contact between the said NMES device and the conductors that are attached to the two electrodes 6a and 6b.
Figure 7B:
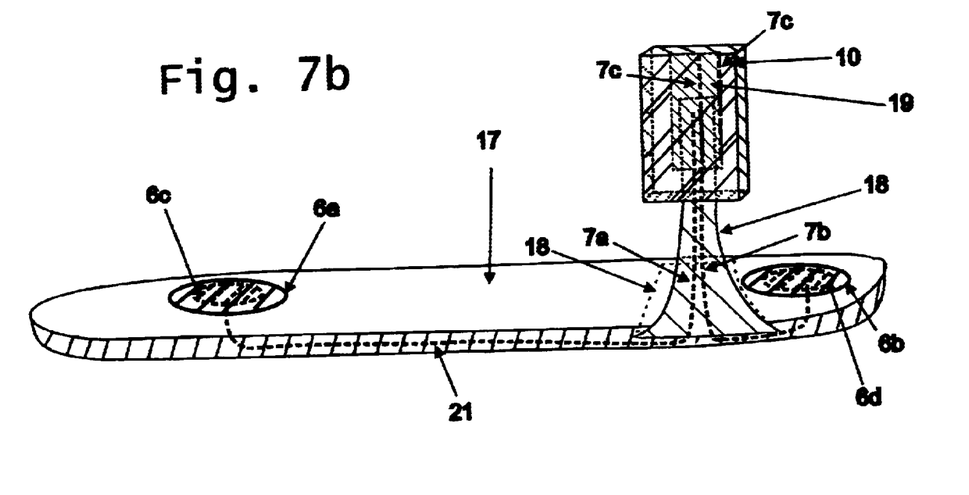

The preferred embodiment of the invention illustrated on FIG. 7a is an footwear insert 17 that allows the quick and convenient method of positioning the electrodes 6a and 6b in the proper areas of the bottom of the foot, as illustrated in FIG. 1. While FIG. 7a illustrates a piece of footwear with a sole 16, it should be understood that the insert can be used with any footwear, including a slipper. This preferred embodiment includes a NMES device 10 that clips 19 onto the side of an item of footwear 15, and slide up and down to rest on the upper edge of the said footwear 15 and to be conveniently removed from the footwear, when not in use. The electrodes 6a and 6b can be of the self-adhering disposable type, to be worn barefoot; or can be of the projecting type illustrated in FIG. 4a, 4b and 4c for use with socks and stockings. The electrodes might also be double-sided as well as self-adhering, in which case the electrodes could be pealed off the insert 17 after some use. The electrodes 6a, 6b would in this case make detachably attached contact with contacts 6c and 6d that are in turn permanently connected to conductors 7a and 7b. as illustrated on FIG. 7b. This means for changing the electrodes 6a, b6, while providing means for connecting to the conductors 7a and 7b, is applicable to electrodes of all types including the projecting electrodes illustrated on FIG. 4a, 4b and 4c. FIG. 7a and 7b also illustrates the means of positioning the NMES device 10 on a tower 18, the base of which is attached or as illustrated, incorporated into the platform 21 of the insert.

Figures 7C, 7D:
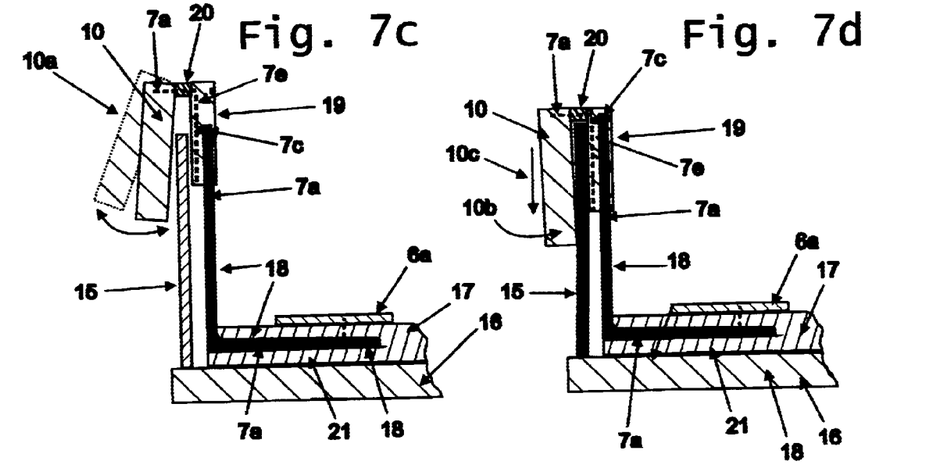
FIGS. 7c, 7d and 7e are cross-sectional views that are details of the insert illustrated in FIG. 7a and 7b.
Figure 7E:
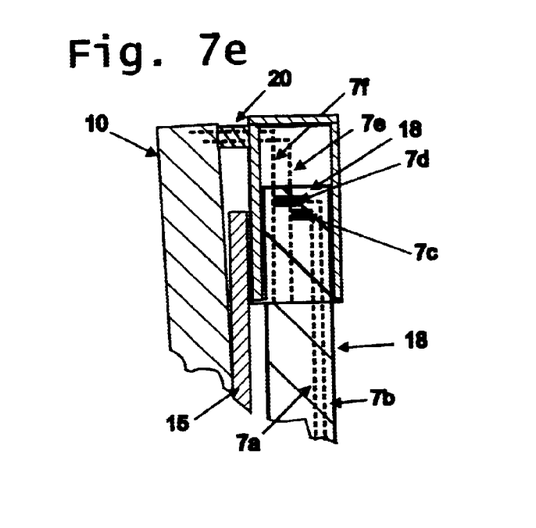

FIG. 7c, 7d and 7e are cross-sectional side views of the clip and slide mechanism of the footwear insert 17, that allows the unit to be placed inside the footwear and secured by clipping on to the side of the upper part of the shoe. FIG. 7c illustrates the clipping action of the preferred embodiment of the invention that is effected by the cooperation of a spring 20 that is attached to the slider 19 and the NMES unit 10. The spring is set so that in its least stressed position it pinches against the slider 19; or if the top of the shoe is between the NMES unit 10 and the slider 19, the spring pinches the top of the shoe between the NMES unit 10 and the slider 19, thereby securing the unit to the side of the shoe. When the wearer wishes to remove the insert 17, he of course can pull the NMES unit 10 away from the slider 19, thereby releasing the shoe. FIG. 7c and 7d also illustrates the sliding action of the slider 19 vertically over the tower 18. This vertical movement in cooperation with the pinching action of the spring allows the NMES unit 10 to fit snuggly around the top edge of the side of the footwear 15.

FIG. 7e illustrates a detail of the same preferred embodiment as illustrated in FIG. 7a, 7b, 7c, and 7d. FIG. 7e illustrates the sliding electrical contacts that allow for the vertical movement of the slider 19 over the tower 18, while still maintaining electrical contact between the electrode 6a and b6 and the NMES unit 10. While slider 19 moves vertically over stationary tower 18, electrically conductive racks 7e and 7f, which are attached to slider 19, slide along contacts 7c and 7d respectively, which are stationary and attached to tower 18, as well as to the conductors 7a and 7b, all the while maintaining electrical contact.

Figure 8:
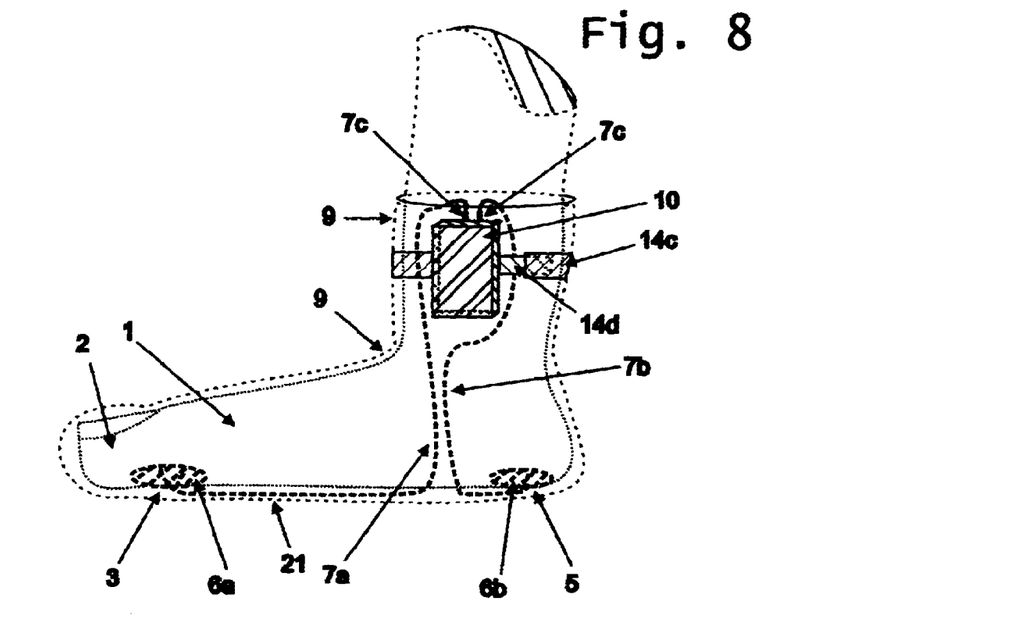
FIG. 8 is a perspective view that illustrates a preferred embodiment of the invention that locates the NMES device 10 on the ankle of the wearer, using a strap 14c, 14d, with a clasp or hook and loop material connector such as VELCRO, while the electrodes 6a, 6b are positioned by being attached to the footwear, or by the wearer directly to his foot.

FIG. 8 illustrates a preferred embodiment of the invention that is similar to that preferred embodiment illustrated in FIG. 5, except that instead of having the NMES unit 10 detachably attached to the footwear, it is rather detachably attached to the leg of the wearer by a strap 14c and 14d which are made of complementary hook and loop fastener material, although other preferred embodiments would include other familiar fastening means. Like the preferred embodiment illustrated in FIG. 5, the electrodes can be attached to the inner surface of the footwear, if of the standard self-adhering type, or from the outside of the footwear through the material from which it is made, using projecting electrodes as illustrated in FIG. 4b, 4b, 4c or other similar electrode. The footwear shown in FIG. 8 can be disposable or retained for repeated use.

Figure 9:
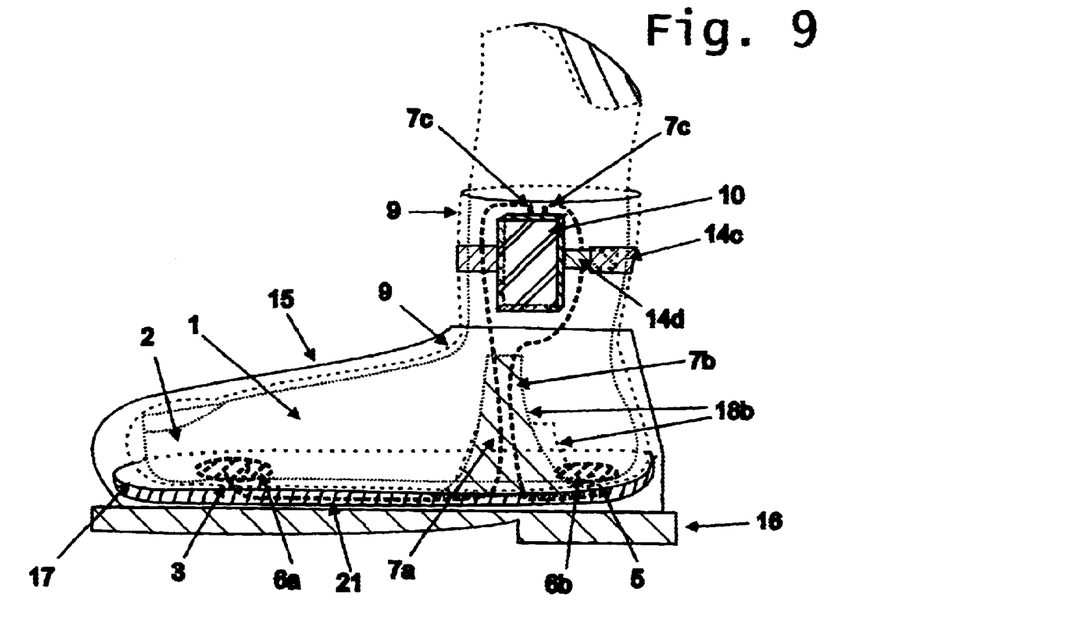
FIG. 9 is a perspective view that illustrates another preferred embodiment of the invention that locates the NMES device 10 on the ankle of the wearer, using a strap 14c, 14d with a clasp or hook and loop material connector such as VELCRO, while the electrodes are positioned by a footwear insert 17, and the conductors are positioned by a tower 18b on the inside of the upper of an item of footwear.

FIG. 9 illustrates a preferred embodiment that includes a footwear insert and is similar to the preferred embodiment illustrated in FIG. 7a, 7b, 7c, 7d, and 7e, except that the NMES unit 10 instead of being detachably attached to the top side of the footwear, is detachably attached in a similar fashion to that preferred embodiment illustrated in FIG. 8, that is it is detachably attached to the leg of the wearer by a strap 14c and 14d which are made of complementary hook and loop fastener material, although other preferred embodiments would include other familiar fastening means. The tower 18b of the preferred embodiment illustrated in FIG. 9 collects the conductors 7a and 7b and passes them up the side of the users foot between sock 9 and footwear 15. The preferred embodiment of FIG. 9 can include all types of electrodes 6a and 6b that are used with the other preferred embodiments, and like them, the footwear need not be a shoe with a sole 16 as illustrated, but can be any type of footwear, including sandals or slippers that can be worn with or without stockings or socks.

While the invention has been described in connection with one item of footwear and reference is made to a single foot, it is to be understood that the method and system that comprise the invention can and in most cases is used on both feet at the same time.

While the invention has been described above in connection with the particular embodiments and examples, one skilled in the art will appreciate that the invention is not necessarily so limited. It will thus be understood that numerous other embodiments, examples, uses, modifications of, and departures from the teachings disclosed may be made, without departing from the scope of the present invention as claimed herein.

For example, it is not necessary that the invention be practiced utilizing the precise pulses per second, ramp up times, stimulus cycles, or stimulus durations. These will vary depending upon the user's health and physiological make-up as well as his special sensitivities. It is therefore apparent that many combinations of electrical stimulus perimeters will achieve successful results so long as the electrodes are placed as hereinbefore described and that the means are provided for doing so, reproducibly, with ease and comfort.

What is claimed is:

1. A method of treatment and prevention of a venous thromboembolic disease associated with reduced blood flow in veins of the calf muscle, the method comprising:
    placing electrodes over or proximal to intrinsic muscles on the plantar surface of a foot of a user, and
    applying electrical current to said electrodes to produce mild contraction of the intrinsic muscles and increasing blood flow in the veins of the calf muscle.

2. The method of claim 1 wherein the electrical current is produced by a single channel sequential Neuromuscular Electrical stimulation (NMES) device.

3. The method of claim 1 wherein the electrical current delivered is in the form of a biphasic symmetrical square wave.

4. The method of claim 1 wherein the electrical current delivered has a frequency of approximately or equal to 50 pulses per second.

5. The method of claim 1 wherein the electrical current delivered has a duration of approximately or equal to 300 microseconds.

6. The method of claim 1 wherein the electrical current is in the form of a pulse with a ramp up time of approximately or equal to 2 seconds and a ramp down time of approximately or equal to 2 seconds.

7. The method of claim 1 wherein the said electrical current is in the form of pulses on a cycle of approximately or equal to 12 seconds "on" and approximately or equal to 48 seconds "off".

8. The method of claim 1 wherein said electrical current delivered is up to 20 milliamperes.

9. The method of claim 1 wherein the user adjusts the intensity of the electrical current to the point needed to produce a minimally visible or palpable muscle contraction in the foot.

10. The method of claim 1, wherein the venous thromboembolic disease is selected from the group consisting of deep vein thrombosis, pulmonary embolism, ankle edema, and venostasis of the calf muscle.

11. The method of claim 10, wherein the venous thromboembolic disease is deep vein thrombosis.

12. A method of treatment and prevention of a venous thromboembolic disease associated with reduced blood flow in veins of the calf muscle, the method comprising:
    placing at least one electrode over or proximal to the heel of a foot of a user,
    placing at least one other electrode over or proximal to intrinsic muscles on the plantar surface of the foot, and
    applying electrical current to said electrodes to produce mild contraction of the intrinsic muscles and increasing blood flow in the veins of the calf muscle.

13. A system for stimulating blood flow velocity in a leg of a user, which includes:
    a platform for substantial direct contact with a bottom of a foot of the user, wherein said substantial direct contact includes contact of the platform with the foot through a garment or material selected from the group consisting of a sock or stocking, and
    said platform includes at least one electrode positioned on the platform for substantial direct contact with the heel of the foot or proximal to the heel, and
    said platform includes at least one electrode positioned on the platform for substantial direct contact with intrinsic muscles on the plantar surface of the foot, or proximal to said intrinsic muscles, and
    the electrodes are connected by conductors to each other and to a neuromuscular electrical stimulation (NMES) unit that generates electrical current for causing the muscles in the foot to mildly contract.

14. A system of claim 13, that includes a single channel sequential NMES unit that generates biphasic symmetrical square wave pulses, and
    with a stimulus frequency of approximately or equal to 50 pulses per second, and
    with a stimulus duration of approximately or equal to 300 microseconds, and
    with a ramp up time of approximately or equal to 2 seconds, and
    a ramp down time of approximately or equal to 2 seconds, and
    the stimulus cycle is set at approximately or equal to 12 seconds on and approximately or equal to 48 seconds off, and
    the user can adjust the intensity to the point needed to produce a minimally visible or palpable muscle contraction in the foot.

15. The system in claim 13, including electrodes having protruding elements that are capable of protruding through a sock or stocking and delivering an electrical current to the bottom of the foot, and such protruding elements being selected from the group consisting of looped or curved elements which can not stick in or pierce the bottom of the foot when the user stands on them, elements which are coated with self-adhering conductive material to enhance adhesion to the skin of the user's foot, and elements which include hook shaped protrusions that act to retain material that is interposed between said platform and the user's foot.

16. The system in claim 13, wherein said platform can be inserted into an item of footwear to be worn on the foot of the user, including a shoe, slipper or sock or forms the sole of an item of footwear, including a shoe, slipper or sock.

17. The system of claim 16, wherein the NMES unit is attachable to the item of footwear.

18. The system of claim 17, wherein said NMES unit can grip an upper of the item of footwear and thereby secure the unit and the connected platform on which the user's foot is in substantial contact.

19. The system of claim 17, wherein the NMES unit is removably attached to the item of footwear.

20. The system of claim 17, further comprising means to permit the NMES to be detachably attached to the top of the item of footwear, on the top of the foot, such that the unit and its setting or settings are clearly visible to the user when the item of footwear is worn by the user.

21. The system of claim 20, wherein said means for detachably attaching the NMES unit to the top of the item of footwear comprises a patch of hook or loop material attached to the NMES unit which is attachable to a complementary patch of loop or hook material, on the top of the item of footwear.

22. The system of claim 17, wherein the system includes means to permit the NMES to be detachably attached to an ankle or leg portion of the item of footwear.

23. The system of claim 13, such that the system includes means to permit the NMES to be detachably attached to the leg of the user, including such means as straps made of complementary hoop and hook material, such as VELCRO™.

24. The system of claim 13, wherein the electrodes are replaceable, being attached to conductive contacts in said platform and being self-adhering on both sides.

25. A system for stimulating blood flow velocity in a leg of a user, which includes:

a platform for substantial direct contact with a bottom of a foot of the user, wherein said substantial direct contact includes contact of the platform with the foot through a garment or material selected from the group consisting of a sock or stocking, and said platform includes a plurality of electrodes positioned on the platform for substantial direct contact with the intrinsic muscles on the plantar surface of the foot, and the electrodes are connected by conductors to each other and to a neuromuscular electrical stimulation (NMES) unit that generates electrical current for causing the muscles in the foot to mildly contract.

* * * * *